(12) United States Patent
Hara et al.

(10) Patent No.: US 10,070,778 B2
(45) Date of Patent: Sep. 11, 2018

(54) ENDOSCOPE SYSTEM, ENDOSCOPE, AND ENDOSCOPE CONNECTOR

(71) Applicant: FUJIFILM Corporation, Tokyo (JP)

(72) Inventors: Kazuyoshi Hara, Kanagawa (JP); Kimitake Fukushima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 242 days.

(21) Appl. No.: 14/724,818

(22) Filed: May 29, 2015

(65) Prior Publication Data
US 2016/0089001 A1    Mar. 31, 2016

(30) Foreign Application Priority Data

Sep. 29, 2014  (JP) .................................. 2014-198944

(51) Int. Cl.
*A61B 1/00* (2006.01)
*A61B 1/05* (2006.01)
(Continued)

(52) U.S. Cl.
CPC ............ *A61B 1/05* (2013.01); *A61B 1/00013* (2013.01); *A61B 1/00016* (2013.01);
(Continued)

(58) Field of Classification Search
CPC ............ A61B 1/00114; A61B 1/00124; A61B 1/00002; A61B 1/00011; A61B 1/00016;
(Continued)

(56) References Cited

U.S. PATENT DOCUMENTS 8,465,330 B2    6/2013  Miyagi et al.
2005/0033116 A1*  2/2005  Miyake .............. G02B 23/2484
                                                            600/109
(Continued)

FOREIGN PATENT DOCUMENTS

CN         102573607         7/2012
JP          4461100          5/2010
(Continued)

OTHER PUBLICATIONS

"Office Action of China Counterpart Application," dated Sep. 1, 2017,with English translation thereof, p. 1-p. 18.

*Primary Examiner* — Alexandra L Newton
*Assistant Examiner* — Pamela F Wu
(74) *Attorney, Agent, or Firm* — JCIPRNET

(57) ABSTRACT

There are provided an endoscope system capable of suppressing an increase in the size of a first connector of an endoscope and of performing non-contact electric power supply and non-contact signal transmission, an endoscope, and an endoscope connector. A power receiving unit and a power supply unit are disposed opposite to each other along an insertion direction of first and second connectors, and an image signal transmission unit and an image signal receiving unit are disposed opposite to each other along the insertion direction of the first and second connectors. A first circuit board is disposed on the opposite side to the power supply unit with respect to the power receiving unit so as to partially overlap the power receiving unit in the insertion direction. The power receiving unit and the image signal transmission unit are disposed so as not to overlap each other in the insertion direction.

18 Claims, 8 Drawing Sheets

(51) Int. Cl.
*A61B 1/015* (2006.01)
*A61B 1/045* (2006.01)

(52) U.S. Cl.
CPC ...... *A61B 1/00029* (2013.01); *A61B 1/00105* (2013.01); *A61B 1/00121* (2013.01); *A61B 1/00126* (2013.01); *A61B 1/015* (2013.01); *A61B 1/045* (2013.01)

(58) Field of Classification Search
CPC ............ A61B 1/00105; A61B 1/00112; A61B 1/00121; A61B 1/00126; A61B 1/00064; A61B 1/00066; A61B 1/00117; A61B 1/00119; A61B 1/00128; A61B 1/126; A61B 1/015; A61B 1/0661; A61B 1/0002; A61B 1/00022; A61B 1/00027; A61B 1/00029; A61B 1/00032; A61B 1/00034; A61B 1/00163; A61B 1/00165; A61B 1/00167; A61B 1/0017; A61B 1/00172; A61B 1/00174; A61B 1/00177; A61B 1/00179; A61B 1/00181; A61B 1/00183; A61B 1/00186; A61B 1/0019; A61B 1/00193; A61B 1/00195; A61B 1/00197; A61B 1/04; A61B 1/05–1/055; A61B 1/06–1/07; A61B 1/00013
USPC .......................................................... 600/109
See application file for complete search history.

(56) References Cited

U.S. PATENT DOCUMENTS

| | | | |
|---|---|---|---|
| 2006/0116550 A1 | 6/2006 | Noguchi et al. | |
| 2006/0293565 A1* | 12/2006 | Uchimura | A61B 1/00016 600/156 |
| 2014/0184771 A1* | 7/2014 | Mazzetti | H02J 5/00 348/75 |
| 2014/0364688 A1* | 12/2014 | Wilson | A61B 1/00013 600/102 |
| 2016/0128549 A1* | 5/2016 | Juergens | A61B 1/00112 600/112 |

FOREIGN PATENT DOCUMENTS

| | | | |
|---|---|---|---|
| JP | 2013-208187 | 10/2013 | |
| WO | WO 2015000554 A1 * | 1/2015 | ......... A61B 1/00112 |

\* cited by examiner

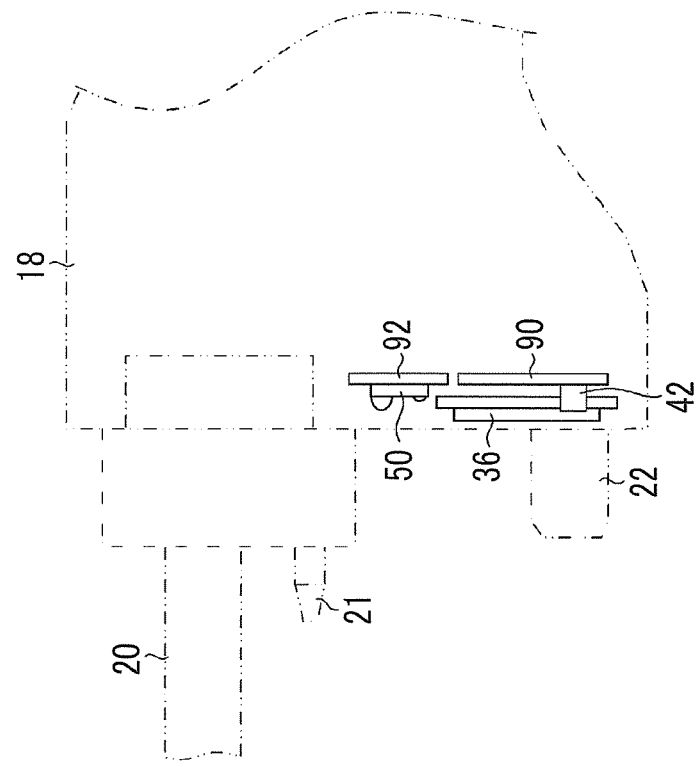
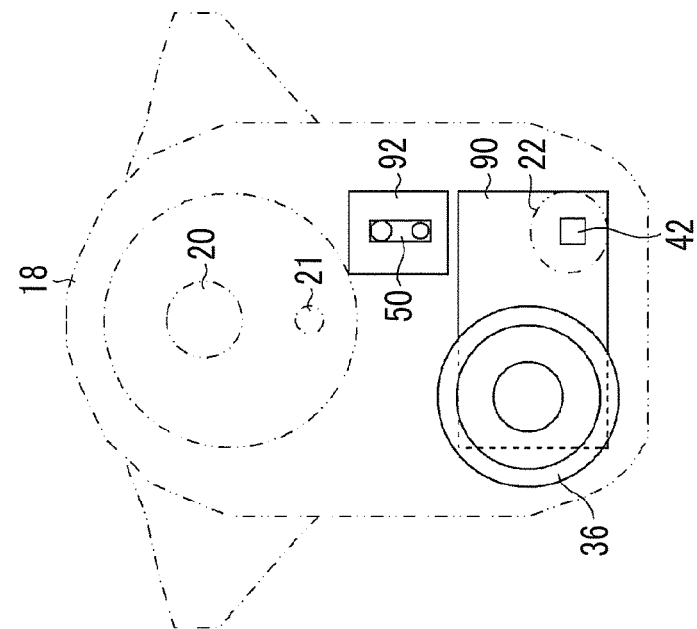

ENDOSCOPE SYSTEM, ENDOSCOPE, AND ENDOSCOPE CONNECTOR

CROSS-REFERENCE TO RELATED APPLICATIONS

The present application claims priority under 35 U.S.C. § 119 to Japanese Patent Application No. 2014-198944, filed on Sep. 29, 2014. The above application is hereby expressly incorporated by reference, in its entirety, into the present application.

BACKGROUND OF THE INVENTION

1. Field of the Invention

The present invention relates to an endoscope system, an endoscope, and an endoscope connector.

2. Description of the Related Art

An endoscope system is configured to include an endoscope and an endoscope processor device. The endoscope includes an image pick-up unit, such as a charge coupled device (CCD) image sensor to image the inside of the body cavity, and a first connector. The endoscope processor device includes a second connector to which the first connector of the endoscope is detachably connected, a control unit for performing image processing and the like on image data output from the endoscope, and a light source. In the endoscope system, the supply of electric power from the endoscope processor device to the endoscope or the transmission of an image signal or a control signal between the endoscope processor device and the endoscope is performed by connecting the first connector of the endoscope and the second connector of the endoscope processor device to each other at an electric contact.

In the endoscope system, it is necessary to perform cleaning and disinfection for the endoscope after use. Therefore, it is necessary to attach a waterproof cap for protecting the electric contact to the first connector of the endoscope. However, not only does it take time and effort to attach and detach the water proof cap, but also there is a problem that the electric contact is damaged when the attachment of the water proof cap is forgotten.

In order to respond to such a problem, JP4461100B discloses an endoscope system that includes electromagnetic induction coupling means in order to perform electric power supply and signal transmission in a non-contact manner between an endoscope and an endoscope processor device. In addition, JP2013-208187A discloses an endoscope system that includes a wireless transmission unit and a wireless receiving unit and a power transmission unit and a power receiving unit in order to perform wireless communication of an image signal and the supply of electric power to an LED light source between an endoscope and an endoscope processor device.

SUMMARY OF THE INVENTION

As disclosed in JP4461100B and JP2013-208187A, in order to perform the supply of electric power and the transmission of a signal in a non-contact manner, it is necessary to arrange a signal transmission device and a power supply device in the first connector of the endoscope and the second connector of the endoscope processor device.

In case of arranging these devices, there is a demand that especially the first connector of the endoscope should not be enlarged, in terms of workability of a user, such as cleaning and disinfection, transportation, and storage, and in terms of maintaining compatibility with existing devices (for example, a cleaning device). For this reason, it is important to arrange the power supply device and the signal transmission device in the first connector so that the first connector of the endoscope is not enlarged.

The invention has been made in view of such a situation, and it is an object of the present invention to provide an endoscope system capable of suppressing an increase in the size of a first connector of an endoscope and of performing non-contact electric power supply and non-contact signal transmission, an endoscope, and an endoscope connector.

According to a first aspect of the invention, there is provided an endoscope system including an endoscope and an endoscope processor device. The endoscope includes an image pick-up unit provided in a distal portion, a light guide for transmitting light to the distal portion, and a first connector that is connected to a second connector of the endoscope processor device in order to perform electric power reception, control signal communication, and image signal communication in a non-contact manner between the endoscope and the endoscope processor device, in which the first connector includes a power receiving unit that receives electric power from a power supply unit in a non-contact manner, a first circuit board on which an image signal transmission unit that transmits an image signal of the image pick-up unit in a non-contact manner is mounted, and a second circuit board on which an endoscope side signal transmission and reception unit that transmits and receives a control signal for controlling the image pick-up unit in a non-contact manner is mounted. The endoscope processor device includes a light source for supplying light to the light guide, a control unit that controls the control signal communication and the image signal communication, and the second connector that is connected to the first connector in order to perform electric power supply, control signal communication, and image signal communication in a non-contact manner between the endoscope processor device and the endoscope. The power receiving unit and the power supply unit are disposed opposite to each other along an insertion direction of the first and second connectors, and the image signal transmission unit and an image signal receiving unit are disposed opposite to each other along the insertion direction of the first and second connectors. The first circuit board is disposed on an opposite side to the power supply unit with respect to the power receiving unit so as to partially overlap the power receiving unit in the insertion direction. The image signal transmission unit is disposed outside a space between the power receiving unit and the power supply unit.

It is preferable that the power supply unit is a primary coil connected to a power source, and the power receiving unit is a secondary coil electromagnetically coupled to the primary coil.

It is preferable that a space between the power receiving unit and the power supply unit is not shielded by a metal member.

It is preferable that the first and second circuit boards are integrally formed into a common circuit board.

It is preferable that a distance between the power receiving unit and the power supply unit is shorter than a distance between the image signal transmission unit and the image signal receiving unit, and is shorter than a distance between the endoscope side signal transmission and reception unit and a processor device side signal transmission and reception unit.

It is preferable that the distance between the image signal transmission unit and the image signal receiving unit is shorter than the distance between the endoscope side signal transmission and reception unit and the processor device side signal transmission and reception unit.

It is preferable that the image signal transmission unit is a laser light emitting element, the image signal receiving unit is a light receiving element, the endoscope side signal transmission and reception unit is formed by an infrared light emitting element and a light receiving element, and the processor device side signal transmission and reception unit is formed by formed by another infrared light emitting element and another light receiving element.

It is preferable that a light guide rod and a shaft for alignment between the image signal transmission unit and the image signal receiving unit are provided, the light guide rod and the shaft protruding from the first connector, and the shaft is disposed on an inner side of a straight line connecting the light guide rod and an exterior of the first connector to each other.

It is preferable that, in the endoscope processor device, the second connector includes a power supply unit that supplies electric power to the power receiving unit in a non-contact manner, an image signal receiving unit that receives a signal from the image signal transmission unit in a non-contact manner, and a processor device side signal transmission and reception unit that transmits and receives a control signal from the endoscope side signal transmission and reception unit in a non-contact manner.

It is preferable that the endoscope processor device includes a third circuit board on which the image signal receiving unit is mounted and a fourth circuit board on which the processor device side signal transmission and reception unit is mounted, and the third circuit board is disposed on an opposite side to the power receiving unit with respect to the power supply unit so as to partially overlap the power supply unit in the insertion direction.

It is preferable that the first connector includes a suction connector, and the suction connector is provided on a side surface of the first connector opposite to the image signal transmission unit when viewed from the insertion direction of the first connector.

According to a second aspect of the invention, there is provided an endoscope including an image pick-up unit provided in a distal portion, a light guide for transmitting light to the distal portion, and a first connector that is connected to a second connector of the endoscope processor device in order to perform electric power reception, control signal communication, and image signal communication in a non-contact manner between the endoscope and the endoscope processor device for driving the image pick-up unit, in which the first connector includes a power receiving unit, a first circuit board on which an image signal transmission unit that transmits an image signal of the image pick-up unit in a non-contact manner is mounted, and a second circuit board on which an endoscope side signal transmission and reception unit that transmits and receives a control signal for controlling the image pick-up unit in a non-contact manner is mounted. The first circuit board is disposed on an opposite side to the power supply unit with respect to the power receiving unit so as to partially overlap the power receiving unit in the insertion direction of the first and second connectors, and the power receiving unit and the image signal transmission unit are disposed so as not to overlap each other in the insertion direction.

According to a third aspect of the invention, there is provided an endoscope connector including a power receiving unit that receives electric power from a power supply unit in a non-contact manner, a first circuit board on which an image signal transmission unit that transmits an image signal in a non-contact manner is mounted, and a second circuit board on which an endoscope side signal transmission and reception unit that transmits and receives a control signal in a non-contact manner is mounted, in which the first circuit board is disposed on an opposite side to the power supply unit with respect to the power receiving unit so as to partially overlap the power receiving unit in the insertion direction of the endoscope connector, and the power receiving unit and the image signal transmission unit are disposed so as not to overlap each other in the insertion direction.

According to the invention, it is possible to suppress an increase in the size of the first connector of the endoscope and to perform non-contact electric power supply and non-contact signal transmission.

BRIEF DESCRIPTION OF THE DRAWINGS

FIGS. 5A and 5B are diagrams for explaining the internal layout of the first connector of the endoscope.

DESCRIPTION OF THE PREFERRED EMBODIMENTS

Figure 1:
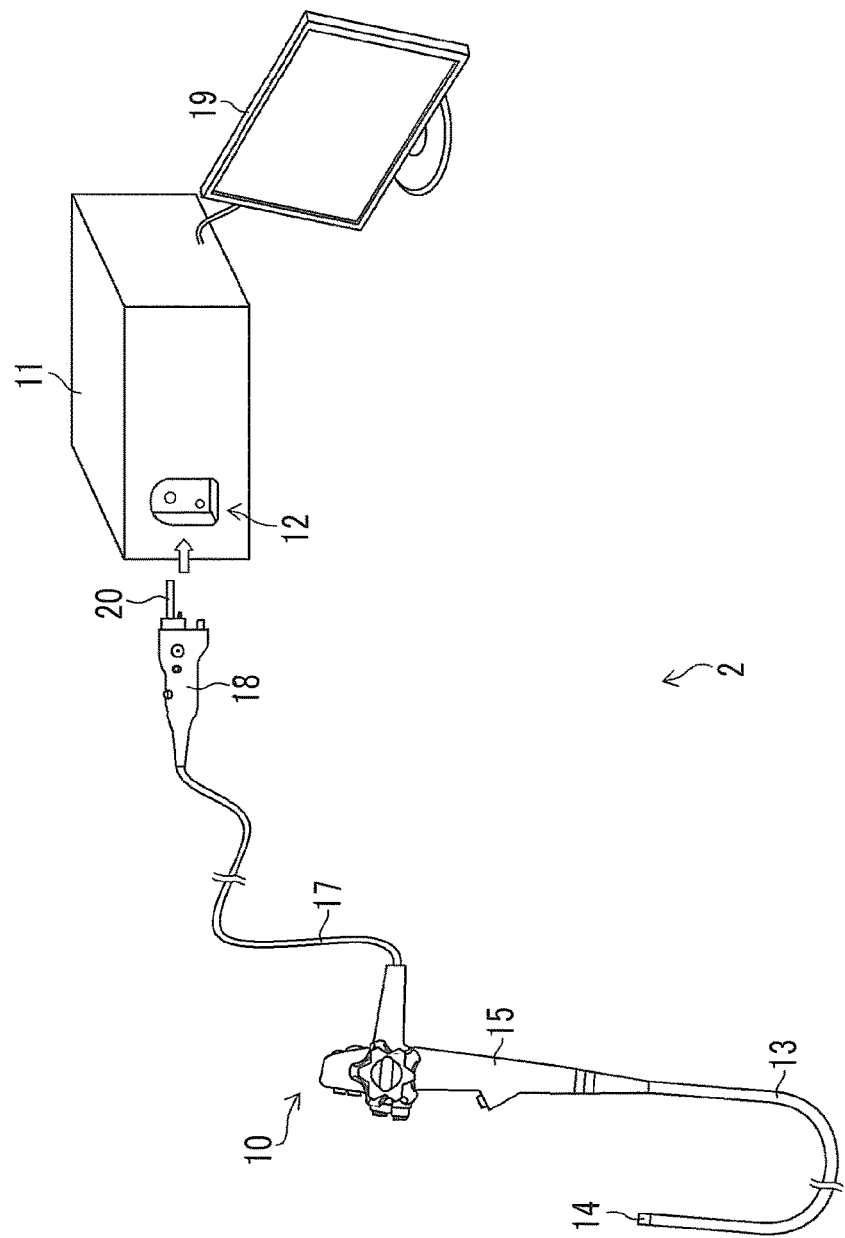
FIG. 1 is an external view showing an endoscope system.

Hereinafter, a preferred embodiment of the invention will be described with reference to the accompanying diagrams. The invention will be described by way of the following preferred embodiment. It is possible to make changes through a number of techniques without departing from the scope of the present invention, and it is possible to use embodiments other than the present embodiment. Accordingly, all changes within the range of the invention are included in the range of the invention.

Here, portions denoted by the same reference numerals in diagrams are the same elements having the same functions. In this specification, when a numerical range is expressed using "~", the values of the upper and lower limits indicated by "~" are assumed to be included in the numerical range.

FIG. 1 is an external view showing an endoscope system to which the invention is applied.

As shown in FIG. 1, an endoscope system 2 includes an endoscope 10 and an endoscope processor device 11.

The endoscope 10 is an example of a flexible endoscope, and includes a flexible insertion part 13 to be inserted into the body cavity of a patient, an operating unit 15 disposed at the proximal end of the insertion part 13, a universal cord 17 disposed in the operating unit 15, and a first connector 18 that is provided at the end of the universal cord 17 and is connected to a second connector 12 of the endoscope processor device 11. However, the endoscope 10 is not limited to the flexible endoscope, and the invention can also be applied to other types of endoscopes, such as a rigid endoscope.

An observation window, an illumination window, and the like are provided on the distal surface of the insertion part 13. An objective optical system that forms subject light from a part to be observed, which is acquired through the observation window, as an optical image, an image pick-up unit that converts the optical image formed by the objective optical system into an electrical signal, and the like are disposed in a distal portion 14 that forms the distal end of the insertion part 13.

The image signal output from the image pick-up unit is transmitted to an image signal transmission unit through a transmission cable that is disposed so as to be inserted into the first connector 18 through the inside of the insertion part 13, the operating unit 15, and the universal cord 17. The image signal is converted into a light signal by the image signal transmission unit, and is optically transmitted to the endoscope processor device 11 in a non-contact manner.

In addition, a light exit part of a light guide to transmit light, which is to be emitted to a part to be observed through the illumination window, is disposed in the distal portion 14. The light guide is disposed so as to be inserted into the first connector 18 through the inside of the insertion part 13, the operating unit 15, and the universal cord 17. A light guide rod 20 connected to the light guide protrudes from the first connector 18.

An angle knob for adjusting the direction of the distal surface of the insertion part 13 in vertical and horizontal directions, an air and water supply button for ejecting air and water from the distal surface of the insertion part 13, a release button for recording an endoscope image as a still image, and the like are provided in the operating unit 15. The direction of the distal surface of the insertion part 13 is adjusted by bending a bending portion provided near the proximal side of the distal portion 14.

The universal cord 17 is covered with a flexible outer wall portion having a long tubular shape. The above-described signal cable, light guide, and air and water supply tube, and the like disposed so as to be inserted into a cavity portion inside the insertion part 13 and a cavity portion inside the operating unit 15 are disposed so as to be inserted into the lumen on the inner side of the outer wall portion.

The first connector 18 is connected to the second connector 12 of the endoscope processor device 11. Between the endoscope 10 and the endoscope processor device 11, supply and reception of electric power, transmission and reception of an image signal, and transmission and reception of a control signal are performed in a non-contact manner through the first connector 18 and the second connector 12. Therefore, as will be described later, a power receiving unit for receiving electric power in a non-contact manner, an image signal transmission unit for optically transmitting the image signal of the image pick-up unit in a non-contact manner, and an endoscope side control signal transmission and reception unit for optically transmitting and receiving a control signal to control the image pick-up unit in a non-contact manner are disposed in the first connector 18.

The second connector 12 is provided in the endoscope processor device 11. As described above, the first connector 18 of the endoscope 10 and the second connector 12 of the endoscope processor device 11 are connected to each other. The endoscope processor device 11 supplies electric power to the endoscope 10, or transmits and receives various signals to and from the endoscope 10.

The endoscope processor device 11 includes a light source. Light from the light source is supplied to the light guide through the light guide rod 20, and the light is transmitted to the distal portion 14 from the light guide.

The endoscope processor device 11 includes a control unit to control the control signal communication and the image signal communication.

A power supply unit for supplying electric power to the power receiving unit of the endoscope 10 in a non-contact manner, an image signal receiving unit for receiving the signal from the image signal transmission unit of the endoscope 10, and a processor device side signal transmission and reception unit for transmitting and receiving the signal from the endoscope side signal transmission and reception unit of the endoscope 10 are disposed in the second connector 12 connected to the first connector 18.

The endoscope processor device 11 includes an input device (not shown; an operating switch, a keyboard, a mouse, and the like). According to the operation of the operator input through the input device, the overall control of the endoscope system 2 is performed.

The endoscope processor device 11 generates image data to form an image (moving image) or still image of a part to be observed by acquiring the image signal output from the image pick-up unit of the distal portion 14 of the endoscope 10 and performing various kinds of signal processing on the acquired image signal. Then, the generated image data is output to a monitor 19 connected through a cable, and the image or the like of the part to be observed is displayed on the monitor 19. In addition, the generated image data is recorded on a recording medium as necessary.

Figure 2:
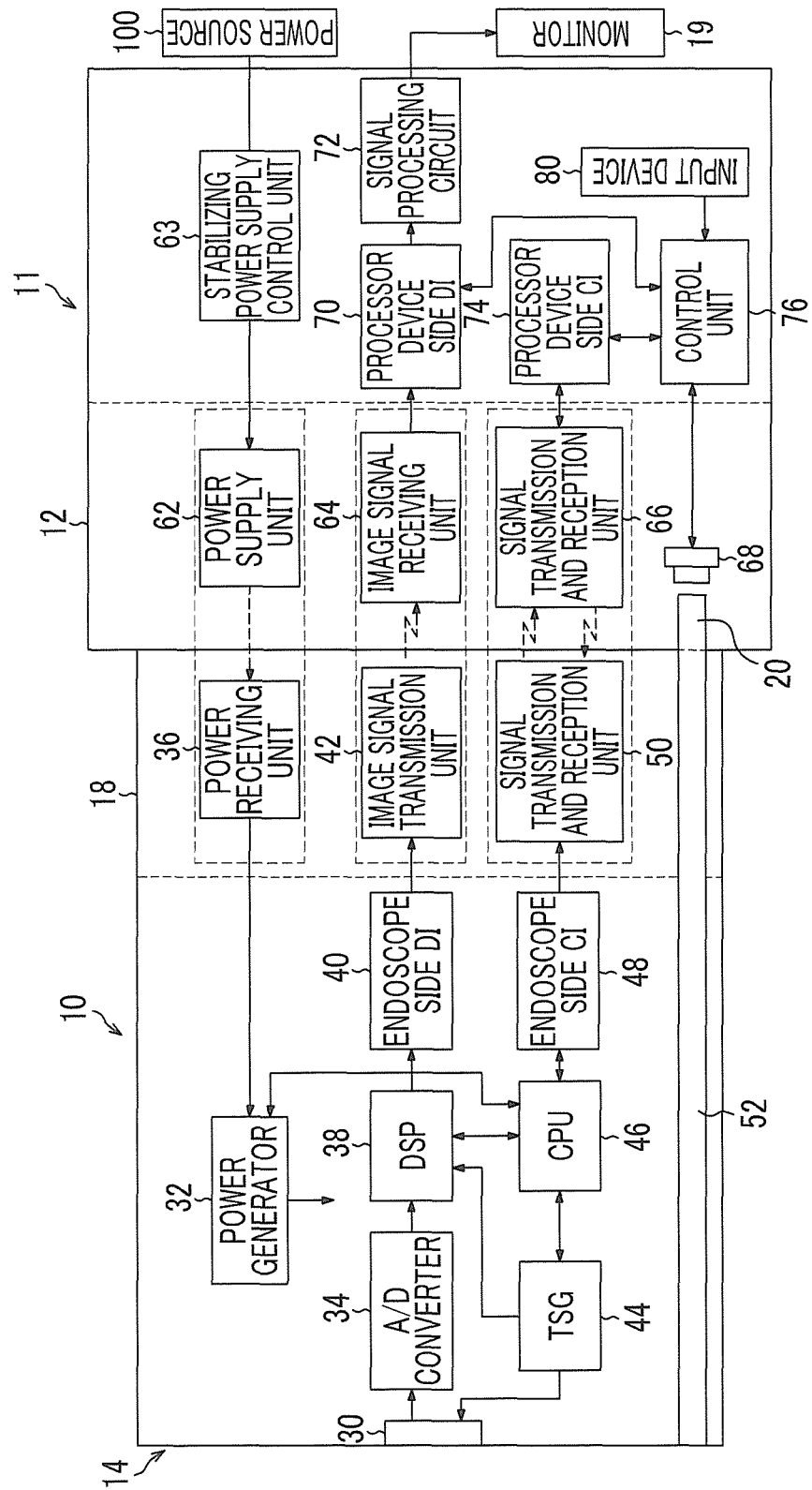
FIG. 2 is a block diagram showing the configuration of the endoscope system.

FIG. 2 is a block diagram showing the configuration of the endoscope system 2 shown in FIG. 1.

The endoscope 10 is detachably connected to the second connector 12 of the endoscope processor device 11 through the first connector 18. In the endoscope system 2 of the present embodiment, the first connector 18 of the endoscope 10 and the second connector 12 of the endoscope processor device 11 are connected to each other, so that the internal circuit of the endoscope 10 and the internal circuit of the endoscope processor device 11 are connected to each other by a non-contact device, such as a transformer or a photocoupler. Therefore, insulation between the internal circuit of the endoscope 10 and the internal circuit of the endoscope processor device 11 is ensured. That is, control signal communication, supply and reception of electric power, and image signal communication can be realized in a non-contact manner.

Electric power required to drive the internal circuit of the endoscope 10 is supplied from the endoscope processor device 11 by non-contact power supply means formed by a power supply unit 62 in the endoscope processor device 11 and a power receiving unit 36 in the endoscope 10. The power receiving unit 36 is disposed in the first connector 18 of the endoscope 10, and the power supply unit 62 is disposed in the second connector 12 of the endoscope processor device 11.

The non-contact power supply means is means for transmitting and receiving electric power in a non-contact manner using electromagnetic coupling. When the first connector 18 of the endoscope 10 is connected to the second connector 12 of the endoscope processor device 11, the power supply unit 62 and the power receiving unit 36 are disposed close to each other so as to be able to be electromagnetically coupled, so that the non-contact transmission of electric power from the power supply unit 62 to the power receiving unit 36 is possible. A commercial power source 100 located outside the endoscope processor device 11 is connected to the power supply unit 62 through a stabilizing power supply control unit 63. Electric power, which is supplied from the commercial power source 100 and is stabilized by the stabilizing power supply control unit 63, is supplied to the power supply unit 62. By the electric power supplied to the power supply unit 62 from the stabilizing power supply control unit 63, non-contact power supply from the power supply unit 62 to the power receiving unit 36 is realized. The power receiving unit 36 receives electric power from the power supply unit 62 in a non-contact manner.

It is preferable that the power supply unit 62 is a primary coil connected to the power source 100 and the power receiving unit 36 is a secondary coil electromagnetically coupled to the primary coil. As the structure of the primary coil and the secondary coil, it is possible to use a structure including a substrate having a plane and a coil wound spirally on the plane.

As the non-contact power supply means, an example in which the power supply unit 62 is a primary coil and the power receiving unit 36 is a secondary coil is shown in the embodiment. However, any means may be used as long as the means can transmit and receive electric power in a non-contact manner.

Here, the electromagnetic coupling means a state in which electric power can be supplied to the other coil (secondary coil) using a magnetic field generated when a current flows through one coil (primary coil) of two coils.

The endoscope 10 includes a power generator 32 connected to the power receiving unit 36, and the power generator 32 can supply electric power to the internal circuit including an image pick-up unit 30 or the like. For example, the power generator 32 receives a current induced in the power receiving unit 36, and generates control power to be supplied to the internal circuit including the image pick-up unit 30 or a central processing unit (CPU) 46, which will be described later, from the input current. The power generator 32 includes a capacitor that is charged by the current induced in the power receiving unit 36 and a voltage stabilizing circuit that generates a desired voltage from the voltage charged in the capacitor.

The image pick-up unit 30 is disposed in the distal portion 14 of the endoscope 10. The image pick-up unit 30 is a device that converts an optical image of a part to be observed, which is acquired through the observation window and is formed by the objective optical system, into an electrical signal and outputs the electrical signal as an image signal as described above. As the image pick-up unit 30, it is possible to use a solid state image pick-up device, such as a charge coupled device (CCD) image sensor or a complementary metal oxide semiconductor (CMOS) image sensor, for example.

In the present embodiment, transmission and reception of the image signal between the endoscope 10 and the endoscope processor device 11 are performed by non-contact optical communication means. The image signal output from the image pick-up unit 30 is transmitted from the endoscope 10 to the endoscope processor device 11 through the first connector 18 and the second connector 12 by non-contact optical transmission. In the present embodiment, in order to process the image signal from the image pick-up unit 30, an analog/digital (A/D) converter 34, a digital signal processor (DSP) 38, a timing signal generator (TSG) 44, and the like are provided. The image signal from the image pick-up unit 30 is converted into the digital signal from the analog signal by an A/D converter 34. The image signal output from the A/D converter 34 is transmitted to the DSP 38. The DSP 38 performs required processing, such as amplification, gamma correction, and white balance processing, on the image signal from the A/D converter 34.

In order to perform non-contact optical transmission between the endoscope 10 and the endoscope processor device 11, for example, the following configuration is provided. The endoscope 10 includes an endoscope side digital interface (DI) 40 connected to the DSP 38 and an image signal transmission unit 42 connected to the endoscope side DI 40. The image signal processed by the DSP 38 is transmitted to the image signal transmission unit 42 through the endoscope side DI 40. Predetermined processing is performed on the image signal from the image pick-up unit 30, and the light signal is transmitted to the endoscope processor device 11 from the image signal transmission unit 42 according to the processed image signal. The image signal transmission unit 42 may be a light emitting device capable of emitting light for optical communication. For example, a laser light emitting element, a light emitting diode, or the like can be used. The laser light emitting element refers to an element capable of emitting laser light that is coherent light, and it is possible to use a gas laser, a solid state laser, a semiconductor laser, and the like.

At least the image signal transmission unit 42 is disposed in the first connector 18 of the endoscope 10. Other devices, for example, the endoscope side DI 40 and the like may be disposed in the first connector 18 of the endoscope 10.

The endoscope processor device 11 includes an image signal receiving unit 64 that receives a light signal from the image signal transmission unit 42, a processor device side DI 70 connected to the image signal receiving unit 64, and a signal processing circuit 72 connected to the processor device side DI 70. The image signal receiving unit 64 is a light receiving device that converts the received light signal into an electrical signal. For example, a light receiving device of a semiconductor device, such as a photodiode or a phototransistor, can be used. The electrical signal from the image signal receiving unit 64 is output to the monitor 19 through the processor device side DI 70 after being subjected to analog processing by the signal processing circuit 72.

In the present embodiment, image signal transmission and reception means based on non-contact optical communication is formed by the image signal transmission unit 42 and the image signal receiving unit 64. For the image signal transmission unit 42 that transmits the image signal of the image pick-up unit 30 in a non-contact manner and the image signal receiving unit 64 that receives the signal from the image signal transmission unit 42 in a non-contact manner, it is possible to use a wireless communication method and a magnetic communication mode without being limited to the non-contact optical communication (optical wireless communication method). The optical wireless communication method refers to a method for transmitting and receiving a signal using infrared rays or the like. The wireless communication method refers to a method for transmitting and receiving a signal by wireless communication (radio waves). The magnetic communication mode refers to a method for transmitting and receiving a signal by providing coils based on the magnetic communication method, generating a modulated signal from the coil on the transmission side as an AC magnetic field, receiving the signal using the coil on the receiving side disposed in the AC magnetic field, and demodulating the signal.

When the first connector 18 of the endoscope 10 is connected to the second connector 12 of the endoscope processor device 11, the image signal transmission unit 42 and the image signal receiving unit 64 are disposed close to each other to allow optical communication therebetween, so that the non-contact optical communication between the image signal transmission unit 42 and the image signal receiving unit 64 is possible.

Transmission and reception of the control signal between the endoscope 10 and the endoscope processor device 11 are performed by non-contact optical communication. In order to control the image pick-up unit 30, the TSG 44 and the CPU 46 are connected to the image pick-up unit 30. Each of the TSG 44 and the CPU 46 outputs a driving signal, which is for making the image pick-up unit 30 acquire an image signal, to the image pick-up unit 30. An endoscope side communication interface (CI) 48 and an endoscope side signal transmission and reception unit 50 are connected to the CPU 46. The endoscope side signal transmission and reception unit 50 is a device capable of optically transmitting and receiving the control signal between the endoscope 10 and the endoscope processor device 11 in a non-contact manner, and includes a light emitting device for optically transmitting the control signal to the endoscope processor device 11 as a light signal and a light receiving device for receiving the control signal from the endoscope processor device 11 as a light signal. As the endoscope side signal transmission and reception unit 50, for example, it is possible to use a non-contact optical data communication unit based on infrared data association (IrDA) that includes an infrared light emitting element for optically transmitting a signal (using infrared rays) and a light receiving element (for example, a photodiode or a phototransistor) for optically receiving a signal. At least the endoscope side signal transmission and reception unit 50 is disposed in the first connector 18 of the endoscope 10. Other devices, for example, the endoscope side CI 48 and the like may be disposed in the first connector 18 of the endoscope 10.

The endoscope processor device 11 includes a processor device side signal transmission and reception unit 66 that optically transmits and receives a control signal between the endoscope 10 and the endoscope side signal transmission and reception unit 50 in a non-contact manner and a processor device side CI 74 connected to the processor device side signal transmission and reception unit 66. The processor device side signal transmission and reception unit 66 is a device capable of optically transmitting and receiving the control signal between the endoscope 10 and the endoscope processor device 11 in a non-contact manner, and includes a light emitting device for optically transmitting the control signal to the endoscope 10 as a light signal and a light receiving device for receiving the control signal from the endoscope 10 as a light signal. As the processor device side signal transmission and reception unit 66, it is possible to use a non-contact optical data communication unit based on infrared data association (IrDA) that includes an infrared light emitting element for optically transmitting a signal (using infrared rays), which is different from the endoscope side signal transmission and reception unit 50, and a light receiving element (for example, a photodiode or a phototransistor) for optically receiving a signal, which is different from the endoscope side signal transmission and reception unit 50. Generally, the infrared ray refers to an electromagnetic wave having a wavelength of 0.7 μm to 1 mm.

When the first connector 18 of the endoscope 10 is connected to the second connector 12 of the endoscope processor device 11, the endoscope side signal transmission and reception unit 50 and the processor device side signal transmission and reception unit 66 are disposed close to each other to allow optical communication therebetween, so that the non-contact optical transmission and reception between the endoscope side signal transmission and reception unit 50 and the processor device side signal transmission and reception unit 66 is possible.

For the endoscope side signal transmission and reception unit 50 that transmits and receives a control signal to control the image pick-up unit 30 in a non-contact manner and the processor device side signal transmission and reception unit 66 that transmits and receives the control signal from the endoscope side signal transmission and reception unit 50 in a non-contact manner, it is possible to use a wireless communication method and a magnetic communication mode without being limited to the non-contact optical communication (optical wireless communication method).

The endoscope processor device 11 includes a light source 68. As the light source 68, it is possible to use a xenon lamp or a semiconductor device, such as a laser diode or a light emitting diode, for example. The endoscope 10 includes a light guide 52. The light guide rod 20 connected to the light guide is provided at the end of the light guide 52. The light guide rod 20 protrudes from the first connector 18, and is connected to the second connector 12 of the endoscope processor device 11. The light source 68 and the light guide rod 20 are aligned, and light from the light source 68 is transmitted to the distal portion 14 through the light guide rod 20 and the light guide 52.

The endoscope processor device 11 includes a control unit 76. The control unit 76 controls the processor device side DI 70 and the like, which form the internal circuit of the endoscope processor device 11, and the light source 68, and controls the entire endoscope system 2 by transmitting a control signal to the CPU 46 and the like that form the internal circuit of the endoscope 10. For example, the endoscope processor device 11 includes an input device 80 (an operating switch, a keyboard, and the like).

A user inputs an instruction for turning ON/OFF of the power source of the endoscope processor device 11 through the input device 80. A control signal based on the instruction input is transmitted to the CPU 46 of the endoscope 10 from the control unit 76 of the endoscope processor device 11 through the non-contact optical communication means formed by the processor device side signal transmission and reception unit 66 and the endoscope side signal transmission and reception unit 50.

A control signal from the CPU 46 is also transmitted to the control unit 76 of the endoscope processor device 11 through the non-contact optical communication means formed by the processor device side signal transmission and reception unit 66 and the endoscope side signal transmission and reception unit 50.

Figure 3:
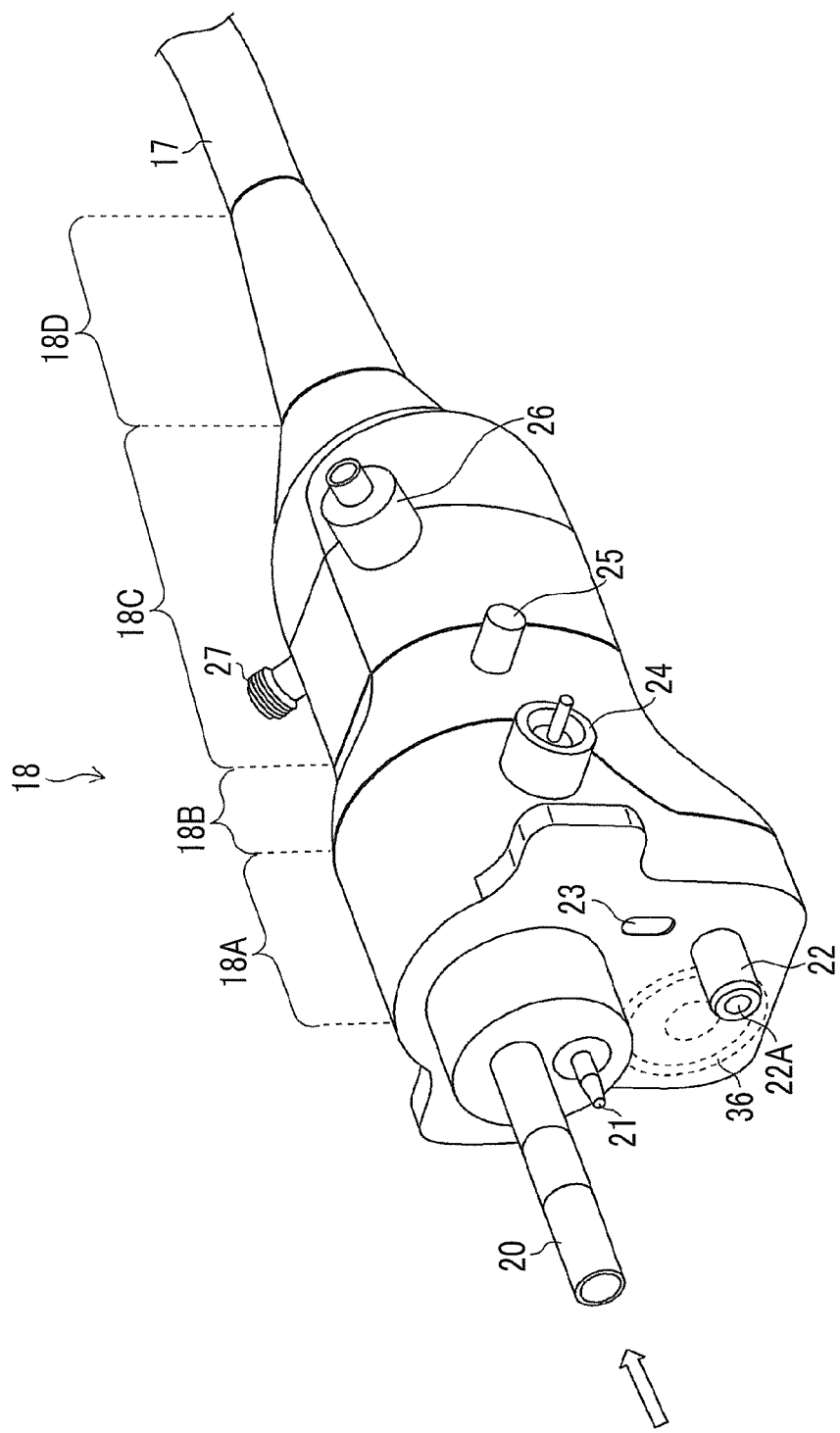
FIG. 3 is an external view of a first connector of an endoscope.

FIG. 3 is an external view of the first connector 18. The first connector 18 of the endoscope 10 is also referred to as an endoscope connector as necessary. As described above, supply and reception of electric power, transmission and reception of an image signal, and transmission and reception of a control signal between the endoscope 10 and the endoscope processor device 11 are performed in a non-contact manner. An electric contact directly connected to the endoscope processor device 11 does not need to be provided in the first connector 18. Accordingly, the first connector 18 can be made to have an electrical insulation property and a waterproof structure covered with a resin having good chemical resistance. By forming the first connector 18 in a waterproof structure, electrical components and the like inside the first connector 18 can be protected against washing water or the like. Accordingly, it is not necessary to attach a separate waterproof cap during the cleaning and disinfection.

As shown in FIG. 3, the first connector 18 includes the light guide rod 20 and a shaft 22 that protrude toward the second connector 12 (not shown) from the first connector 18.

The first connector 18 can be configured to include a first connector case 18A, a second connector case 18B, a third connector case 18C, and a cover rubber 18D sequentially from the side connected to the second connector 12 of the endoscope processor device 11, for example.

The light guide rod 20 protrudes toward the second connector 12 (in an insertion direction) from the first connector case 18A having a connection surface with respect to the second connector 12. Below the light guide rod 20, an air cap 21 is provided so as to be almost parallel to the light guide rod 20. The air cap 21 communicates with an air and water supply conduit disposed in the endoscope 10 in order to supply air and water to the distal portion 14 of the endoscope 10.

The shaft 22 protrudes from the connection surface of the first connector case 18A along the insertion direction with respect to the second connector 12. The shaft 22 is used for alignment between the image signal transmission unit 42 of the endoscope 10 and the image signal receiving unit 64 of the endoscope processor device 11. In particular, the image signal transmission unit 42 is disposed in the extending direction of the central axis of the shaft 22. A window 22A is provided at the distal end of the shaft 22, so that light can be transmitted therethrough. Through the window 22A, optical transmission and reception of image signals between the image signal transmission unit 42 and the image signal receiving unit 64 are performed in a non-contact manner.

On the connection surface of the first connector case 18A, a window 23 is provided at a position corresponding to the endoscope side signal transmission and reception unit 50. Through the window 23, optical transmission and reception of control signals between the endoscope side signal transmission and reception unit 50 and the processor device side signal transmission and reception unit 66 are performed in a non-contact manner.

In the first connector case 18A, the power receiving unit 36 is disposed at a position close to the connection surface of the first connector case 18A. Since the power receiving unit 36 is disposed inside the first connector case 18A, the power receiving unit 36 is not exposed to the outside.

An air and water supply connector 24 is provided on the side surface of the first connector case 18A. The air and water supply connector 24 is connected to a water supply tank (not shown). By operating the air and water supply button of the operating unit 15, air and water can be supplied to the distal portion 14. Dirt on the lens surface of the distal portion 14 is removed by the water supplied to the distal portion 14. In addition, it is possible to expand the patient's lumen or to remove the water droplets on the lens with the air supplied to the distal portion 14.

In addition, a suction connector (not shown) is disposed on the side surface of the first connector case 18A opposite to the air and water supply connector 24. By connecting a tube to the suction connector, communication with a suction device (not shown) can be made. By operating the suction button of the operating unit 15 in a state in which the suction device is driven, it is possible to suck a lesion or the like through the forceps opening of the distal portion 14.

In the present embodiment, the suction connector is provided on the side surface of the first connector 18 opposite to the image signal transmission unit 42 when the first connector 18 is viewed from the insertion direction (viewed from the direction of the arrow in FIG. 3). That is, the suction connector is disposed on the side surface of the first connector 18 far from the shaft 22. Through the configuration, for example, even if a lesion comes out of the suction connector when the tube is detached from the suction connector, it is possible to suppress the contamination of the window 22A of the shaft 22. On the other hand, since the suction connector is disposed on the side surface of the first connector 18 close to the power receiving unit 36, a lesion may be attached through the suction connector. Since the region of the first connector 18 where the power receiving unit 36 is disposed is a plane, cleaning such as wiping can be easily performed.

For example, a balloon connector 25 is provided on the side surface of the second connector case 18B. By connecting a tube to the balloon connector 25, it is possible to inflate and deflate a balloon (not shown) provided in the insertion part 13. In the case of the endoscope 10 in which no balloon is provided in the insertion part 13, it is not necessary to provide the balloon connector 25 in the first connector 18.

An auxiliary water supply connector (not shown) is disposed on the side surface of the second connector case 18B opposite to the balloon connector 25. By connecting a tube to the auxiliary water supply connector, it is possible to supply water to the distal portion 14 of the endoscope 10. By the water supplied to the distal portion 14 through the auxiliary water supply connector, foreign matter adhering to the body cavity, blood generated during the endoscopic operation, and the like are washed out.

A ventilation connector 26 is provided on the side surface of the third connector case 18C. The ventilation connector 26 is used for the leak test to check the air leakage of the insertion part 13. The ventilation connector 26 communicates with the inside of the first connector 18. Since the inside of the first connector 18 communicates with the inside of each of the universal cord 17, the operating unit 15, and the insertion part 13, the ventilation connector 26 communicates with the inside of the insertion part 13.

In addition, an S connector 27 is disposed on the side surface of the third connector case 18C opposite to the ventilation connector 26. The S connector 27 is a terminal for connection with an S cord for returning a high-frequency current, which leaks to the endoscope 10 when using an electrosurgical device (electric scalpel), to the control unit of the electrosurgical device, for example.

The cover rubber 18D is disposed at a position where the end of the third connector case 18C is covered. The universal cord 17 protrudes from the cover rubber 18D.

Figure 4:
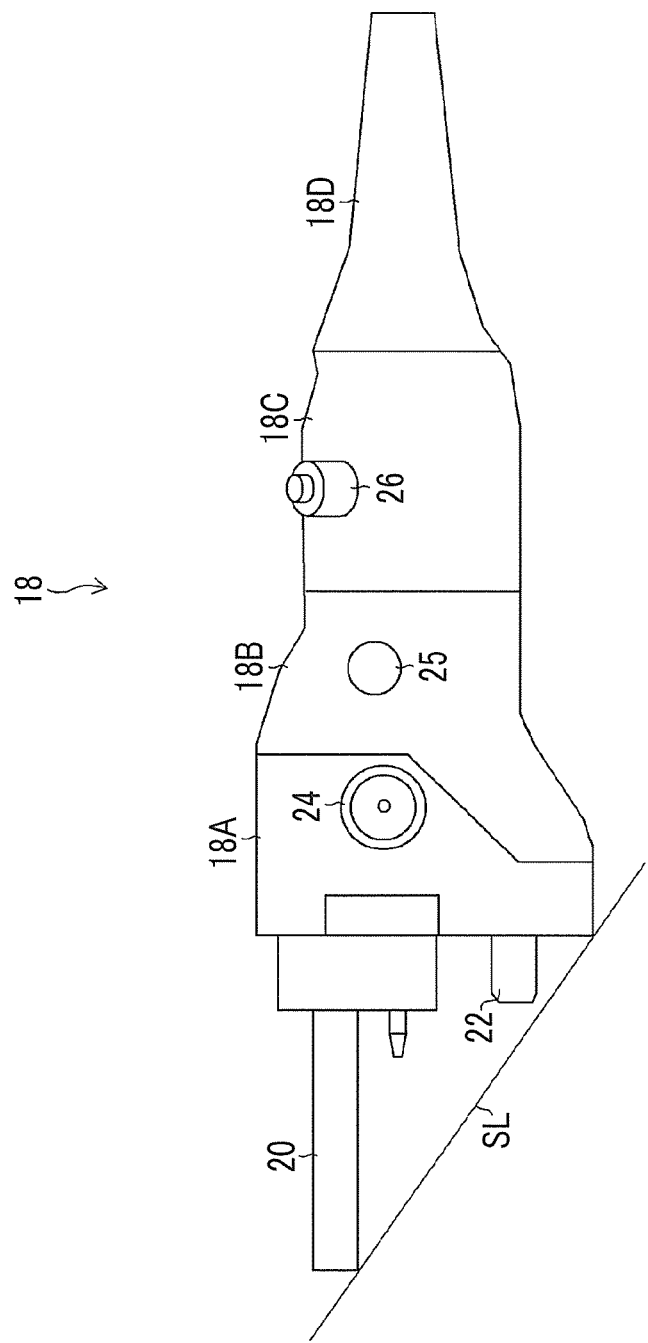
FIG. 4 is a side view of the first connector of the endoscope.

FIG. 4 is a side view of the first connector. In the present embodiment, as the positional relationship among the light guide rod 20, the shaft 22, and the exterior of the first connector 18, it is preferable that the shaft 22 is disposed on the inner side of a straight line SL connecting the light guide rod 20 and the exterior of the first connector 18 to each other. By arranging the shaft 22 on the inner side of the straight line SL connecting the distal end of the light guide rod 20 to the exterior of the first connector 18 on a side where the shaft 22 is formed, it is possible to prevent the shaft 22 from coming in contact with the floor even when the first connector 18 is dropped, for example. Therefore, it is possible to prevent the shaft 22 from being damaged.

FIGS. 5A and 5B are diagrams for explaining the internal layout of the first connector 18 of the endoscope 10. FIG. 5A is a diagram when the first connector 18 is viewed from the insertion direction, and FIG. 5B is a diagram when the first connector 18 is viewed from the side surface. As shown in FIGS. 5A and 5B, the image signal transmission unit 42 is mounted on a first circuit board 90. The first circuit board 90 is a substrate for supporting the image signal transmission unit 42, and is a substrate having wiring lines that are electrically connected to the image signal transmission unit 42. A rigid substrate, a flexible substrate, and the like can be used as the first circuit board 90. The image signal transmission unit 42 is formed by a laser light emitting element, for example.

The endoscope side signal transmission and reception unit 50 is mounted on a second circuit board 92. The second circuit board 92 is a substrate for supporting the endoscope side signal transmission and reception unit 50, and is a substrate having wiring lines that are electrically connected to the endoscope side signal transmission and reception unit 50. Similar to the first circuit board 90, a rigid substrate, a flexible substrate, and the like can be used as the second circuit board 92. The endoscope side signal transmission and reception unit 50 is formed by the IrDA, for example.

The power receiving unit 36 includes a ferrite substrate and a coil wound on the ferrite substrate, for example. As shown in FIG. 5B, the power receiving unit 36 is disposed so as to be closer to the connection surface of the first connector 18 than the first circuit board 90, on which the image signal transmission unit 42 is mounted, and the second circuit board 92, on which the endoscope side signal transmission and reception unit 50 is mounted, are. That is, the first circuit board 90 is disposed on the opposite side to a power supply unit (not shown) with respect to the power receiving unit 36 as will be described later.

In addition, as shown in FIG. 5A, the first circuit board 90 is disposed so as to partially overlap the power receiving unit 36 in the insertion direction of the first connector 18 and the second connector 12. The first circuit board 90 on which the image signal transmission unit 42 is mounted has a large area since a laser light emitting element, a laser light emitting element driver, a peripheral circuit, a protection circuit, a connector, and the like are mounted thereon. For example, the size of the first circuit board 90 is 20 mm to 40 mm×20 mm to 40 mm. Also in the power receiving unit 36, a certain degree of size is required when receiving electric power in a non-contact manner. For example, the power receiving unit 36 has a size of φ20 mm to φ50 mm. In the present embodiment, by arranging the first circuit board 90 and the power receiving unit 36 so as to partially overlap each other in the insertion direction, it is possible to suppress an increase in the size of the first connector 18 in the width direction, that is, the size increase of the first connector 18 when viewed from the insertion direction.

Even if the first circuit board 90 and the power receiving unit 36 are disposed so as to partially overlap each other in the insertion direction as in the present embodiment, the size of the first connector 18 in the longitudinal direction is small as shown in the side view of FIG. 5B. This is because the thicknesses of the power receiving unit 36 and the first circuit board 90 are relatively small.

The power receiving unit 36 and the image signal transmission unit 42 are disposed so as not to overlap each other in the insertion direction. This is to prevent the light signal from the image signal transmission unit 42 from being blocked by the power receiving unit 36.

On the other hand, unlike in the present embodiment, for example, in the insertion direction of the first connector 18 and the second connector 12, when the first circuit board 90 and the power receiving unit 36 are disposed so as not to overlap each other along the insertion direction and the power receiving unit 36 and the first circuit board 90 are disposed side by side when viewed from the insertion direction, the size of the first connector 18 in the width direction is increased. The increase in the size of the first connector 18 of the endoscope 10 in the width direction is not preferable in terms of workability of a user, such as cleaning and disinfection, transportation, and storage, and in terms of maintaining compatibility with existing devices (for example, a cleaning device).

Figure 6A:
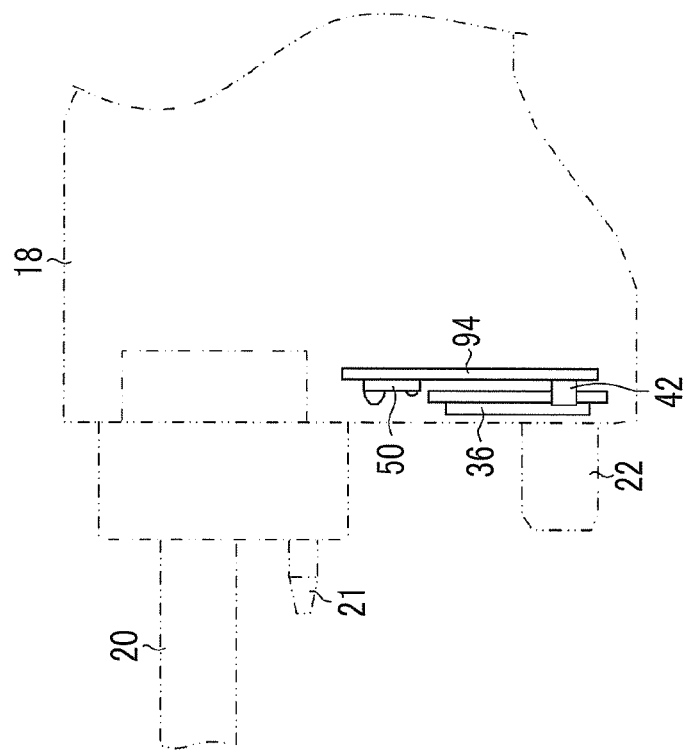
FIGS. 6A and 6B are diagrams for explaining another internal layout of the first connector of the endoscope.
Figure 6B:
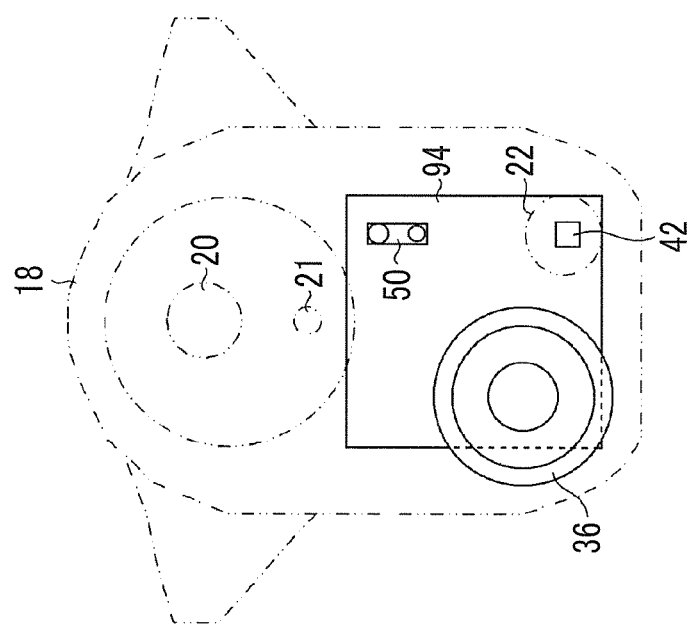

FIGS. 6A and 6B are diagrams for explaining another internal layout of the first connector 18 of the endoscope 10. FIG. 6A is a diagram when the first connector 18 is viewed from the insertion direction, and FIG. 6B is a diagram when the first connector 18 is viewed from the side surface. In the internal layout of the first connector 18 of the endoscope 10 shown in FIGS. 6A and 6B, the image signal transmission unit 42 and the endoscope side signal transmission and reception unit 50 are mounted on a common circuit board 94 that is integrally formed. Here, the common circuit board 94 is a substrate for supporting the image signal transmission unit 42 and the endoscope side signal transmission and reception unit 50, and is a substrate having wiring lines that are electrically connected to the image signal transmission unit 42 and the endoscope side signal transmission and reception unit 50. A rigid substrate, a flexible substrate, and the like can be used as the common circuit board 94. For example, the size of the common circuit board 94 is 30 mm to 50 mm×30 mm to 50 mm. Not only the laser light emitting element, the laser light emitting element driver, the peripheral circuit, and the protection circuit described above but also an infrared communication element, an infrared communication driver, a peripheral circuit, and a connector that form the endoscope side signal transmission and reception unit 50 are mounted on the common circuit board 94.

By using the common circuit board 94, the number of circuit boards used in the first connector 18 can be reduced compared with the case where the first circuit board 90 and the second circuit board 92 shown in FIGS. 5A and 5B are used. Since the number of components for fixing the common circuit board 94 to the first connector 18 and space can be reduced by using the common circuit board 94, it is possible to suppress an increase in the size of the first connector 18.

Figure 7:
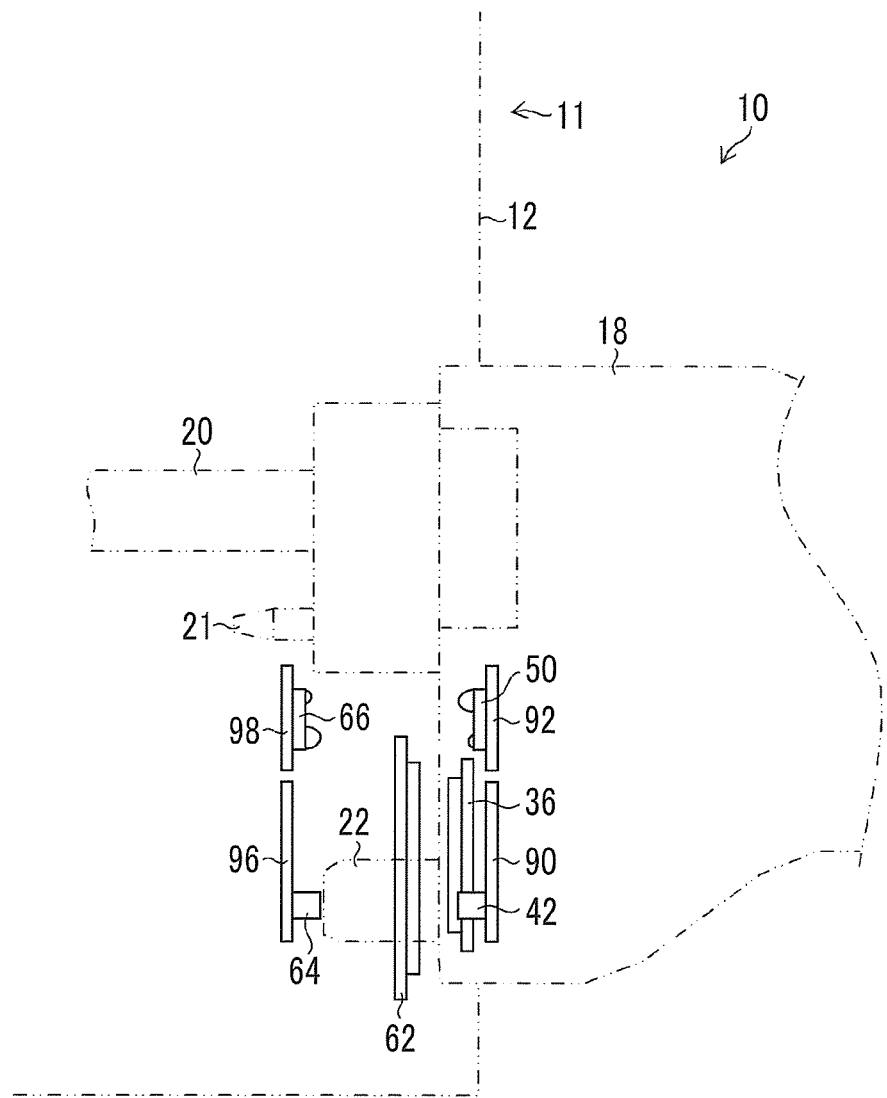
FIG. 7 is an explanatory diagram showing a state in which the first connector of the endoscope and a second connector of an endoscope processor device are connected to each other.

FIG. 7 is an explanatory diagram showing a state in which the first connector 18 of the endoscope 10 and the second connector 12 of the endoscope processor device 11 are connected to each other. As shown in FIG. 7, the first connector 18 of the endoscope 10 includes the power receiving unit 36, the first circuit board 90 on which the image signal transmission unit 42 is mounted, and the second circuit board 92 on which the endoscope side signal transmission and reception unit 50 is mounted. As shown in FIG. 7, the first circuit board 90 is disposed on the opposite side to the power supply unit 62 with respect to the power receiving unit 36, and is disposed so as to partially overlap the power receiving unit 36 in the insertion direction as shown in FIGS. 5A and 5B.

The second connector 12 includes the power supply unit 62, a third circuit board 96 on which the image signal receiving unit 64 is mounted, and a fourth circuit board 98 on which the processor device side signal transmission and reception unit 66 is mounted.

The third circuit board 96 is a substrate for supporting the image signal receiving unit 64, and is a substrate having wiring lines that are electrically connected to the image signal receiving unit 64. The fourth circuit board 98 is a substrate for supporting the processor device side signal transmission and reception unit 66, and is a substrate having wiring lines that are electrically connected to the processor device side signal transmission and reception unit 66. A rigid substrate, a flexible substrate, and the like can be used as the third circuit board 96 and the fourth circuit board 98.

The image signal receiving unit 64 is a light receiving element, and is formed by a photodiode, for example. The processor device side signal transmission and reception unit 66 is formed by the IrDA, for example.

The power supply unit 62 is disposed so as to be closer to the connection surface of the first connector 18 than the third circuit board 96 is. That is, the third circuit board 96 is disposed on the opposite side to the power receiving unit 36 with respect to the power supply unit 62. The third circuit board 96 is disposed so as to partially overlap the power supply unit 62 in the insertion direction of the first connector 18 and the second connector 12. This is to match the configuration of the first connector 18. Through such a configuration, it is possible to suppress an increase in the size of the second connector 12 in the width direction.

The power receiving unit 36 and the power supply unit 62 are disposed opposite to each other along the insertion direction of the first connector 18 and the second connector 12, and the image signal transmission unit 42 and the image signal receiving unit 64 are disposed opposite to each other along the insertion direction of the first connector 18 and the second connector 12. By arranging these units opposite to each other along the insertion direction, it is possible to efficiently transmit and receive electric power between the power receiving unit 36 and the power supply unit 62 and to transmit and receive an image signal between the image signal transmission unit 42 and the image signal receiving unit 64. In the present embodiment, the image signal transmission unit 42 is disposed anywhere other than the space between the power receiving unit 36 and the power supply unit 62. Since the image signal transmission unit 42 does not shield the space between the power receiving unit 36 and the power supply unit 62 disposed opposite to each other, it is possible to prevent the image signal transmission unit 42 from being influenced by the magnetic flux between the power receiving unit 36 and the power supply unit 62.

The endoscope side signal transmission and reception unit 50 and the processor device side signal transmission and reception unit 66 are disposed opposite to each other along the insertion direction of the first connector 18 and the second connector 12. More specifically, the light emitting element of the endoscope side signal transmission and reception unit 50 and the light receiving element of the processor device side signal transmission and reception unit 66 are disposed opposite to each other, and the light receiving element of the endoscope side signal transmission and reception unit 50 and the light emitting element of the processor device side signal transmission and reception unit 66 are disposed opposite to each other.

As shown in FIG. 7, the distance between the power receiving unit 36 and the power supply unit 62 is shorter than the distance between the image signal transmission unit 42 and the image signal receiving unit 64 and the distance between the endoscope side signal transmission and reception unit 50 and the processor device side signal transmission and reception unit 66. These distances are determined in consideration of non-contact supply and reception of electric power, non-contact transmission and reception of an image signal, and non-contact transmission and reception of a control signal. Here, each of the distances means the shortest distance.

For example, the distance between the power receiving unit 36 and the power supply unit 62 is 10 mm or less, and the distance between the image signal transmission unit 42 and the image signal receiving unit 64 and the distance between the endoscope side signal transmission and reception unit 50 and the processor device side signal transmission and reception unit 66 is greater than 10 mm and equal to or less than 25 mm. However, the distances are not limited thereto. As shown in FIG. 7, the space between the power receiving unit 36 and the power supply unit 62 is not shielded by a metal member. Since the space between the power receiving unit 36 and the power supply unit 62 is not shielded by a metal member, a problem, such as the generation of heat in the metal member, does not occur. Here, the shielding includes a case in which a part of the space between the power receiving unit 36 and the power supply unit 62 is shielded.

Figure 8:
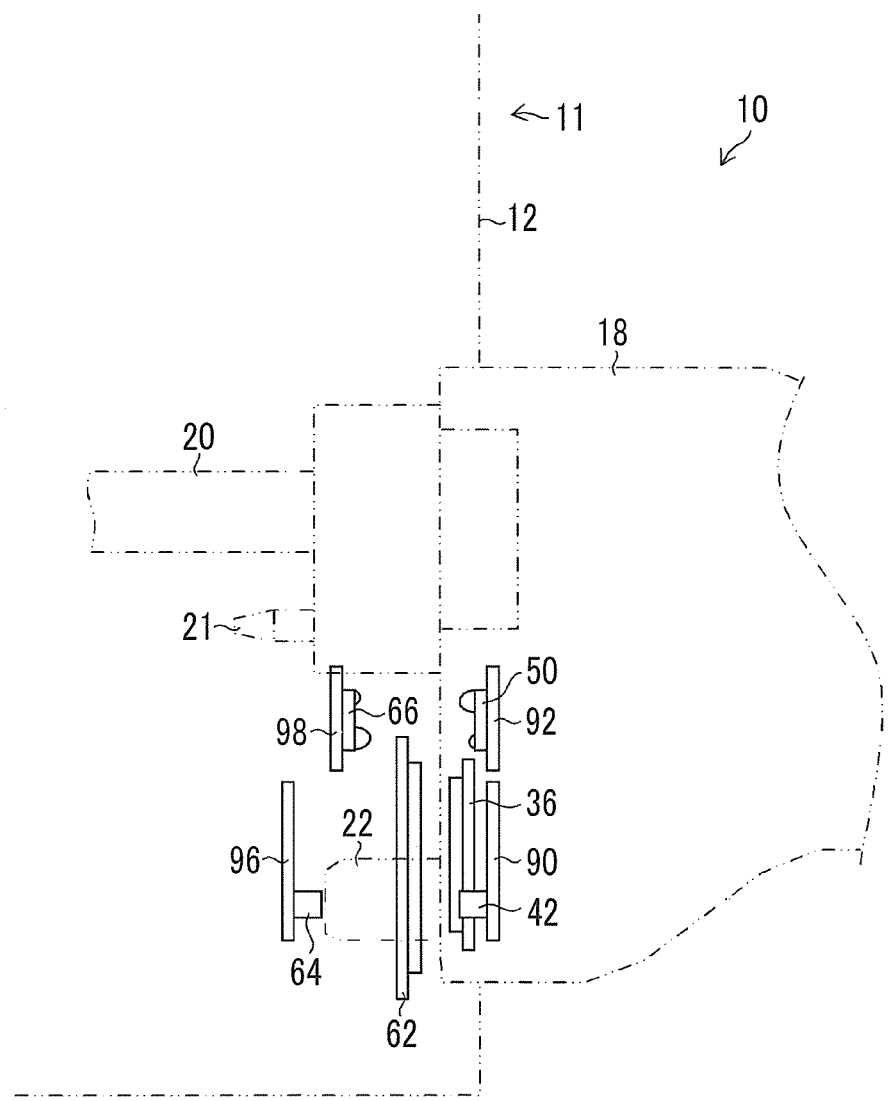
FIG. 8 is an explanatory diagram showing another state in which the first connector of the endoscope and the second connector of the endoscope processor device are connected to each other.

FIG. 8 is an explanatory diagram showing another state in which the first connector 18 of the endoscope 10 and the second connector 12 of the endoscope processor device 11 are connected to each other. The relationship among the distance between the power receiving unit 36 and the power supply unit 62, the distance between the image signal transmission unit 42 and the image signal receiving unit 64, and the distance between the endoscope side signal transmission and reception unit 50 and the processor device side signal transmission and reception unit 66 are different from that in the embodiment shown in FIG. 7.

As shown in FIG. 8, the distance between the power receiving unit 36 and the power supply unit 62 is shorter than the distance between the image signal transmission unit 42 and the image signal receiving unit 64 and the distance between the endoscope side signal transmission and reception unit 50 and the processor device side signal transmission and reception unit 66, and the distance between the image signal transmission unit 42 and the image signal receiving unit 64 is shorter than the distance between the endoscope side signal transmission and reception unit 50 and the processor device side signal transmission and reception unit 66. For example, the distance between the power receiving unit 36 and the power supply unit 62 is 10 mm or less, the distance between the endoscope side signal transmission and reception unit 50 and the processor device side signal transmission and reception unit 66 is greater than 10 mm and equal to or less than 15 mm, and the distance between the image signal transmission unit 42 and the image signal receiving unit 64 is greater than 15 mm and equal to or less than 25 mm. However, the distances are not limited thereto.

What is claimed is:

1. An endoscope system, comprising:
an endoscope; and
an endoscope processor device,
wherein the endoscope includes an image pick-up unit provided in a distal portion, a light guide for transmitting light to the distal portion, and a first connector that is connected to a second connector of the endoscope processor device in order to perform electric power reception, control signal communication, and image signal communication in a non-contact manner between the endoscope and the endoscope processor device, the first connector includes a power receiving unit that receives electric power from a power supply unit in a non-contact manner, a first circuit board on which an image signal transmission unit that transmits an image signal of the image pick-up unit in a non-contact manner is mounted, and a second circuit board on which an endoscope side signal transmission and reception unit that transmits and receives a control signal for controlling the image pick-up unit in a non-contact manner is mounted, and the endoscope processor device includes a light source for supplying light to the light guide, a control unit that controls the control signal communication and the image signal communication, and the second connector that is connected to the first connector in order to perform electric power supply, control signal communication, and image signal communication in a non-contact manner between the endoscope processor device and the endoscope, wherein the power receiving unit and the power supply unit are disposed opposite to each other along an insertion direction of the first and second connectors, and the image signal transmission unit and an image signal receiving unit are disposed opposite to each other along the insertion direction of the first and second connectors, and the first circuit board is disposed on an opposite side to the power supply unit with respect to the power receiving unit so as to partially overlap the power receiving unit in the insertion direction, and the image signal transmission unit is disposed outside a space between the power receiving unit and the power supply unit, wherein a normal direction of the first circuit board is parallel to the insertion direction of the first and second connectors.

2. The endoscope system according to claim 1, wherein the power supply unit is a primary coil connected to a power source, and the power receiving unit is a secondary coil electromagnetically coupled to the primary coil.

3. The endoscope system according to claim 2, wherein a space between the power receiving unit and the power supply unit is not shielded by a metal member.

4. The endoscope system according to claim 3, wherein the first and second circuit boards are integrally formed into a common circuit board.

5. The endoscope system according to claim 2, wherein the first and second circuit boards are integrally formed into a common circuit board.

6. The endoscope system according to claim 2, wherein a distance between the power receiving unit and the power supply unit is shorter than a distance between the image signal transmission unit and the image signal receiving unit, and is shorter than a distance between the endoscope side signal transmission and reception unit and a processor device side signal transmission and reception unit.

7. The endoscope system according to claim 1, wherein a space between the power receiving unit and the power supply unit is not shielded by a metal member.

8. The endoscope system according to claim 7, wherein the first and second circuit boards are integrally formed into a common circuit board.

9. The endoscope system according to claim 7, wherein a distance between the power receiving unit and the power supply unit is shorter than a distance between the image signal transmission unit and the image signal receiving unit, and is shorter than a distance between the endoscope side signal transmission and reception unit and a processor device side signal transmission and reception unit.

10. The endoscope system according to claim 1, wherein the first and second circuit boards are formed by a common circuit board that is integrally formed.

11. The endoscope system according to claim 1, wherein a distance between the power receiving unit and the power supply unit is shorter than a distance between the image signal transmission unit and the image signal receiving unit, and is shorter than a distance between the endoscope side signal transmission and reception unit and a processor device side signal transmission and reception unit.

12. The endoscope system according to claim 11, wherein the distance between the image signal transmission unit and the image signal receiving unit is shorter than the distance between the endoscope side signal transmission and reception unit and the processor device side signal transmission and reception unit.

13. The endoscope system according to claim 11, wherein the image signal transmission unit is a laser light emitting element, the image signal receiving unit is a light receiving element, the endoscope side signal transmission and reception unit is formed by an infrared light emitting element and a light receiving element, and the processor device side signal transmission and reception unit is formed by another infrared light emitting element and another light receiving element.

14. The endoscope system according to claim 1, wherein a light guide rod and a shaft for alignment between the image signal transmission unit and the image signal receiving unit are provided, the light guide rod and the shaft protruding from the first connector, and the shaft is disposed such that the shaft does not interfere with a straight line, which is over the shaft, connecting the distal end of the light guide rod and an exterior of the first connector on a side where the shaft is formed.

15. The endoscope system according to claim 1, wherein, in the endoscope processor device, the second connector includes a power supply unit that supplies electric power to the power receiving unit in a non-contact manner, an image signal receiving unit that receives a signal from the image signal transmission unit in a non-contact manner, and a processor device side signal transmission and reception unit that transmits and receives a control signal from the endoscope side signal transmission and reception unit in a non-contact manner.

16. The endoscope system according to claim 15, wherein the endoscope processor device includes a third circuit board on which the image signal receiving unit is mounted and a fourth circuit board on which the processor device side signal transmission and reception unit is mounted, and the third circuit board is disposed on an opposite side to the power receiving unit with respect to the power supply unit so as to partially overlap the power supply unit in the insertion direction.

17. The endoscope system according to claim 1, wherein the first connector includes a suction connector, and the suction connector is provided on a side surface of the first connector opposite to the image signal transmission unit when viewed from the insertion direction of the first connector.

18. The endoscope system according to claim 1, wherein the power receiving unit comprises a substrate and a coil wound on the substrate, the power receiving unit is formed with a disc-shaped structure, and a normal direction of the power receiving unit is parallel to the insertion direction of the first and second connectors.

\* \* \* \* \*